United States Patent
Flohr et al.

(10) Patent No.: US 7,304,058 B2
(45) Date of Patent: Dec. 4, 2007

(54) CARBAMIC ACID ESTERS OF BENZOTHIAZOLES

(75) Inventors: Alexander Flohr, Basel (CH); Roland Jakob-Roetne, Inzlingen (DE); Roger David Norcross, Rheinfelden (CH); Claus Riemer, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 499 days.

(21) Appl. No.: 10/848,436

(22) Filed: May 18, 2004

(65) Prior Publication Data
US 2004/0235842 A1    Nov. 25, 2004

(30) Foreign Application Priority Data
May 21, 2003  (EP)  ................... 03011090

(51) Int. Cl.
| | | |
|---|---|---|
| *A61K 31/428* | (2006.01) | |
| *A61K 31/5377* | (2006.01) | |
| *C07D 277/62* | (2006.01) | |
| *C07D 413/04* | (2006.01) | |
| *C07D 417/04* | (2006.01) | |

(52) U.S. Cl. ............ 514/233.8; 544/106; 544/111; 544/133; 544/135; 548/146; 548/152; 548/161; 514/231.2; 514/233.5; 514/365; 514/367

(58) Field of Classification Search ......... 544/106, 544/111, 132, 133, 135; 514/231.2, 231.5, 514/233.5, 233.8, 365, 367; 548/146, 152, 548/161
See application file for complete search history.

(56) References Cited

U.S. PATENT DOCUMENTS 6,521,754 B2 * 2/2003 Alanine et al. ............. 544/129
6,734,179 B2 * 5/2004 Flohr et al. ............... 514/233.8
6,835,732 B2 * 12/2004 Alanine et al. .......... 514/235.5
6,963,000 B2 * 11/2005 Alanine et al. ............. 548/146

FOREIGN PATENT DOCUMENTS

| WO | WO 01/97786 A2 | 12/2001 |
|---|---|---|
| WO | WO 03/053946 A1 | 7/2003 |

OTHER PUBLICATIONS

Alanine et al (2001): STN International HCAPLUS database, Columbus (Ohio), accession No. 2001:935384.*

* cited by examiner

*Primary Examiner*—Golam M. M. Shameem
(74) *Attorney, Agent, or Firm*—George J. Johnston; Patricia S. Rocha-Tramaloni; Gene J. Yao

(57) ABSTRACT

The present invention relates to a compound of formula I

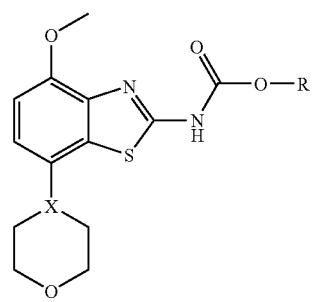

wherein R, X and n are defined hereinabove, and to a pharmaceutically acceptable salt thereof. The compound may be used for the treatment of diseases related to the A2A receptor.

19 Claims, No Drawings

CARBAMIC ACID ESTERS OF BENZOTHIAZOLES

FIELD OF THE INVENTION

The present invention relates to compounds of the general formula

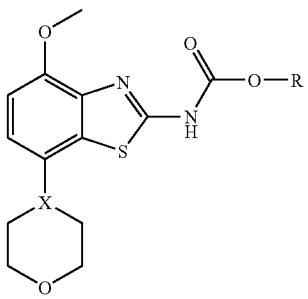

wherein R, X and n are described hereinbelow. These ligands (compounds) have a good affinity to the $A_{2A}$-receptor and a high selectivity to the $A_1$- and $A_3$ receptors. These compounds are useful, inter alia, in treatment of Alzheimer's disease, depression, Parkinson's disease and ADHD.

BACKGROUND OF THE INVENTION

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzym A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtypes has been classically characterized by the adenylate cyclase effector system, which utilizes CAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326-328 amino acids) was cloned from various species (canine, human, rat, dog, chick, bovine, guinea-pig) with 90-95% sequence identify among the mammalian species. The $A_{2A}$ receptor (409-412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317-320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The action of both subtypes is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioral state and (patho) physiological conditions. Under conditions of increased demand and decreased availability of energy (such as hypoxia, hypoglycemia, and/or excessive neuronal activity), adenosine provides a powerful protective feedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents.

Adenosine antagonists stimulate the activity of the CNS and have proven to be effective as cognition enhancers. Selective $A_{2a}$ antagonists have therapeutic potential in the treatment of various forms of dementia, for example in Alzheimer's disease, and of neurodegenerative disorders, e.g. stroke. Adenosine $A_{2a}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyper-activity disorder).

An important role for adenosine in the cardiovascular system is as a cardioprotective agent. Levels of endogenous adenosine increase in response to ischaemia and hypoxia, and protect cardiac tissue during and after trauma (preconditioning). By acting at the $A_1$ receptor, adenosine $A_1$ agonists may protect against the injury caused by myocardial ischemia and reperfusion. The modulating influence of $A_2a$ receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricula arrhytmias.

Adenosine modulates many aspects of renal function, including renin release, glomerular filtration rate and renal blood flow. Compounds which antagonise the renal affects of adenosine have potential as renal protective agents. Furthermore, adenosine $A_3$ and/or $A_{2B}$ antagonists may be useful in the treatment of asthma and other allergic responses or and in the treatment of diabetes mellitus and obesity.

Numerous documents describe the current knowledge on adenosine receptors. These include Bioorganic & Medicinal Chemistry, 6, (1998), 619-641; Bioorganic & Medicinal Chemistry, 6, (1998), 707-719; J. Med. Chem., (1998), 41, 2835-2845; J. Med. Chem., (1998), 41, 3186-3201; J. Med. Chem., (1998), 41, 2126-2133; J. Med. Chem., (1999), 42,706-721; J. Med. Chem., (1996), 39, 1164-1171 Arch. Pharm. Med. Chem., 332, 39-41, (1999); Am. J. Physiol., 276, H1113-1116, (1999) and Naunyn Schmied, Arch. Pharmacol. 362, 375-381, (2000).

SUMMARY OF THE INVENTION

An aspect of the present invention is directed to a compound of formula I

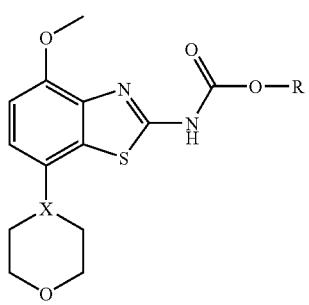

wherein,
R is selected from the group consisting of
  cyclopentyl,
  cyclopentyl substituted by hydroxy,
  cyclohexyl,
  cyclohexyl substituted by hydroxy,
  ethyl,
  isobutyl,
  methoxyethyl,
  tetrahydropyran-4-yl,
  —$(CH_2)_n$-tetrahydrofuran-2-yl,
  —$(CH_2)_n$-tetrahydrofuran-3-yl, and
  5-hydroxy-bicyclo[2.2.1]hept-2-yl;

X is selected from CH and N; and
n is 0 or 1;
or a pharmaceutically acceptable salt thereof.

Other embodiments of this invention are directed to methods of manufacturing compounds of formula I, pharmaceutical compositions containing a compound of formula I, and a pharmaceutically acceptable salt thereof, as well as a method of controlling or prevention of illnesses based on the modulation of the adenosine system, such as Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse comprising administering to a patient a therapeutically effective amount of a compound of formula I or a pharmaceutically acceptable salt thereof.

Furthermore, compounds of the present invention are useful as sedatives, muscle relaxants, antipsychotics, antiepileptics, anticonvulsants and cardioprotective agents for disorders such as coronary artery disease and heart failure. Preferred indications in accordance with the present invention are those that depend on the $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION OF THE INVENTION

The term "pharmaceutically acceptable acid addition salts" refers to aces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

The term therapeutically effective amount" refers to an amount of at least one compound of formula I, or a pharmaceutically acceptable salt thereof, that modulates adenosine.

The present invention is related to a compound of formula I

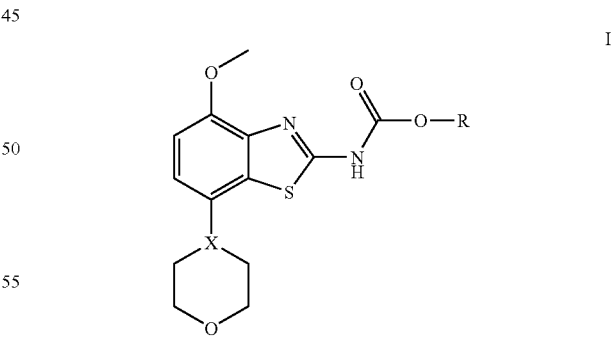

wherein,
R is selected from the group consisting of
  cyclopentyl,
  cyclopentyl substituted by hydroxy,
  cyclohexyl,
  cyclohexyl substituted by hydroxy,
  ethyl,
  isobutyl, methoxyethyl,
tetrahydropyran-4-yl,
—(CH$_2$)$_n$-tetrahydrofuran-2-yl,
—(CH$_2$)$_n$-tetrahydrofuran-3-yl, and
5-hydroxy-bicyclo[2.2.1]hept-2-yl;
X is selected from CH and N; and
n is 0 or 1;
or a pharmaceutically acceptable salt thereof.

In another embodiment, this invention relates to a compound of formula I

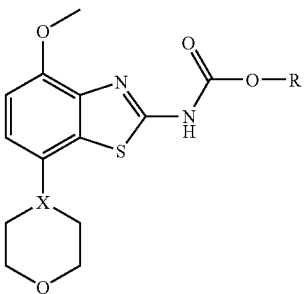

I wherein
R is selected from the group consisting of
  cyclohexyl substituted by hydroxy,
  ethyl,
  —(CH$_2$)$_n$-tetrahydrofuran-2-yl, and
  —(CH$_2$)$_n$-tetrahydrofuran-3-yl;
X is CH; and
n is 0 or 1;
or a pharmaceutically acceptable salt thereof.

In another embodiment, this invention relates to a compound of formula I

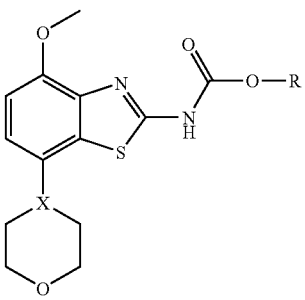

I wherein
R is selected from the group consisting of
  cyclopentyl substituted by hydroxy,
  cyclohexyl,
  cyclohexyl substituted by hydroxy,
  isobutyl,
  methoxyethyl,
  tetrahydropyran-4-yl,
  —(CH$_2$)$_n$-tetrahydrofuran-3-yl, and
  5-hydroxy-bicyclo[2.2.1]hept-2-yl;
X is N; and
n is 0 or 1;
or a pharmaceutically acceptable salt thereof.

In a preferred embodiment, the compound of formula I is where R is cyclohexyl substituted by hydroxy, and X is CH.

In another preferred embodiment, the compound of formula I is where R is ethyl, and X is CH.

In another preferred embodiment, the compound of formula I is where R is —(CH$_2$)$_n$-tetrahydrofuran-2-yl, and X is CH.

In another preferred embodiment, the compound of formula I is where R is —(CH$_2$)$_n$-tetrahydrofuran-3-yl, and X is CH.

In another preferred embodiment, the compound of formula I is where R is cyclopentyl substituted by hydroxy, and X is N.

In another preferred embodiment, the compound of formula I is where R is cyclohexyl, and X is N.

In another preferred embodiment, the compound of formula I is where R is cyclohexyl substituted by hydroxy, and X is N.

In another preferred embodiment, the compound of formula I is where R is isobutyl, and X is N.

In another preferred embodiment, the compound of formula I is where R is methoxyethyl, and X is N.

In another preferred embodiment, the compound of formula I is where R is tetrahydropyran-4-yl, and X is N.

In another preferred embodiment, the compound of formula I is where R is —(CH$_2$)$_n$-tetrahydrofuran-3-yl, and X is N.

In another preferred embodiment, the compound of formula I is where R is 5-hydroxy-bicyclo[2.2.1]hept-2-yl, and X is N.

Preferred compounds of the present application are compounds of formula I, wherein R is cyclopentyl, cyclopentyl substituted by hydroxy, cyclohexyl and cyclohexyl substituted by hydroxy, for example the following compounds:
(trans)-[4-methoxy-7-(tetrahydro-pyran-4-yl)-benzothiazol-2-yl]-carbamic acid 4-hydroxy-cydohexyl ester,
(4-methoxy-7-morpholin-4-yl-benzothiazol-2-yl)-carbamic acid cyclohexyl ester,
(trans)-(4-methoxy-7-morpholin-4-yl-benzothiazol-2-yl)-carbamic acid 4-hydroxy-cydohexyl ester,
(cis)-(4-methoxy-7-morpholin-4-yl-benzothiazol-2-yl)-carbamic acid 4-hydroxy-cyclohexyl ester or
(cis/trans)- (4-methoxy-7-morpholin-4-yl-benzothiazol-2-yl)-carbamic acid 3-hydroxy-cyclopentyl ester.

Preferred are further compounds of formula I, wherein R is ethyl, isobutyl, or methoxyethyl, for example the following compounds:
[4-methoxy-7-(tetrahydro-pyran-4-yl)-benzothiazol-2-yl]-carbamic acid ethyl ester,
(4-methoxy-7-morpholin-4-yl-benzothiazol-2-yl)-carbamic acid 2-methoxy-ethyl ester or
(4-methoxy-7-morpholin-4-yl-benzothiazol-2-yl)-carbamic acid isobutyl ester.

Preferred compounds of the present application are compounds of formula I, wherein R is tetrahydropyran-4-yl or —(CH$_2$),-tetrahydrofuran-2 or 3-yl, for example the following compounds:
(4-methoxy-7-morpholin-4-yl-benzothiazol-2-yl)-carbamic acid tetrahydro-pyran-4-yl ester,
(R)-(4-methoxy-7-morpholin-4-yl-benzothiazol-2-yl)-carbamic acid tetrahydro-furan-3-yl ester,
[4-methoxy-7-(tetrahydro-pyran-4-yl)-benzothiazol-2-yl]-carbamic acid tetrahydro-furan-2-yl-methyl ester or
[4-Methoxy-7-(tetrahydro-pyran-4-yl)-benzothiazol-2-yl]-carbamic acid (S)-(tetrahydro-furan-3-yl) ester.

Preferred are further compounds of formula I, wherein R is 5-hydroxy-bicyclo[2.2.1]hept-2-yl, for example the following compound:

(rac)-(exo,exo)-(4-methoxy-7-morpholin-4-yl-benzothiazol-2-yl)-carbamic acid 5-hydroxy-bicyclo[2.2.1]hept-2-yl ester.

One aspect of the present compounds of formula I and their pharmaceutically acceptable salts can be prepared by methods known in the art, for example, by processes described below, which process comprises reacting a compound of formula

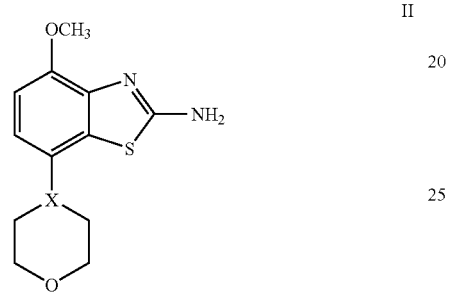

II with a compound of formula

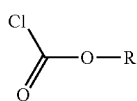

III to produce a compound of formula

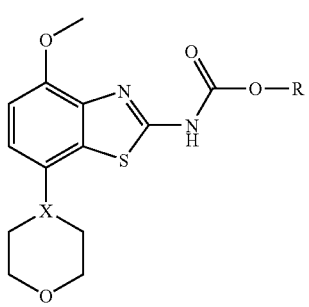

I wherein R and X are defined above, and if desired, converting the compounds obtained into pharmaceutically acceptable salts.

Another aspect of the present compounds of formula I and their pharmaceutically acceptable salts can be prepared by methods known in the art, for example, by processes described below, which process comprises reacting a compound of formula

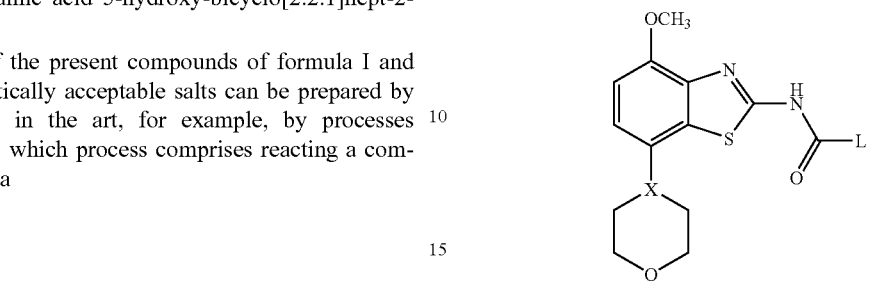

IV with a compound of formula

HO—R    V to produce a compound of formula

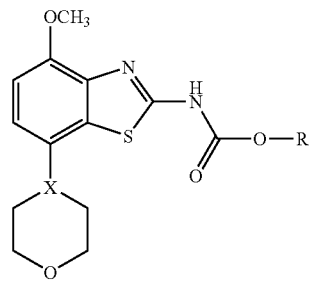

I wherein R and X are as defined above, L is a leaving group such as halogen, —O-phenyl or O-lower alkyl, and if desired, converting the compounds obtained into pharmaceutically acceptable salts.

In Examples 1-13 and in the following schemes 1 and 2 the preparation of compounds of formula I are described in more detail.

The starting materials are known compounds or may be prepared according to methods known in the art.

Preparation of Compounds of Formula I

The intermediates 7-(morpholin-4-yl)-4-methoxy-benzothiazol-2-ylamine and 7-(tetrahydropyran-4-yl)-4-methoxy-benzothiazol-2-ylamine may be prepared according to methods disclosed in WO01/97786. The preparation of compounds of formula (I) using the intermediate of formula (II) is also described in WO01/97786.

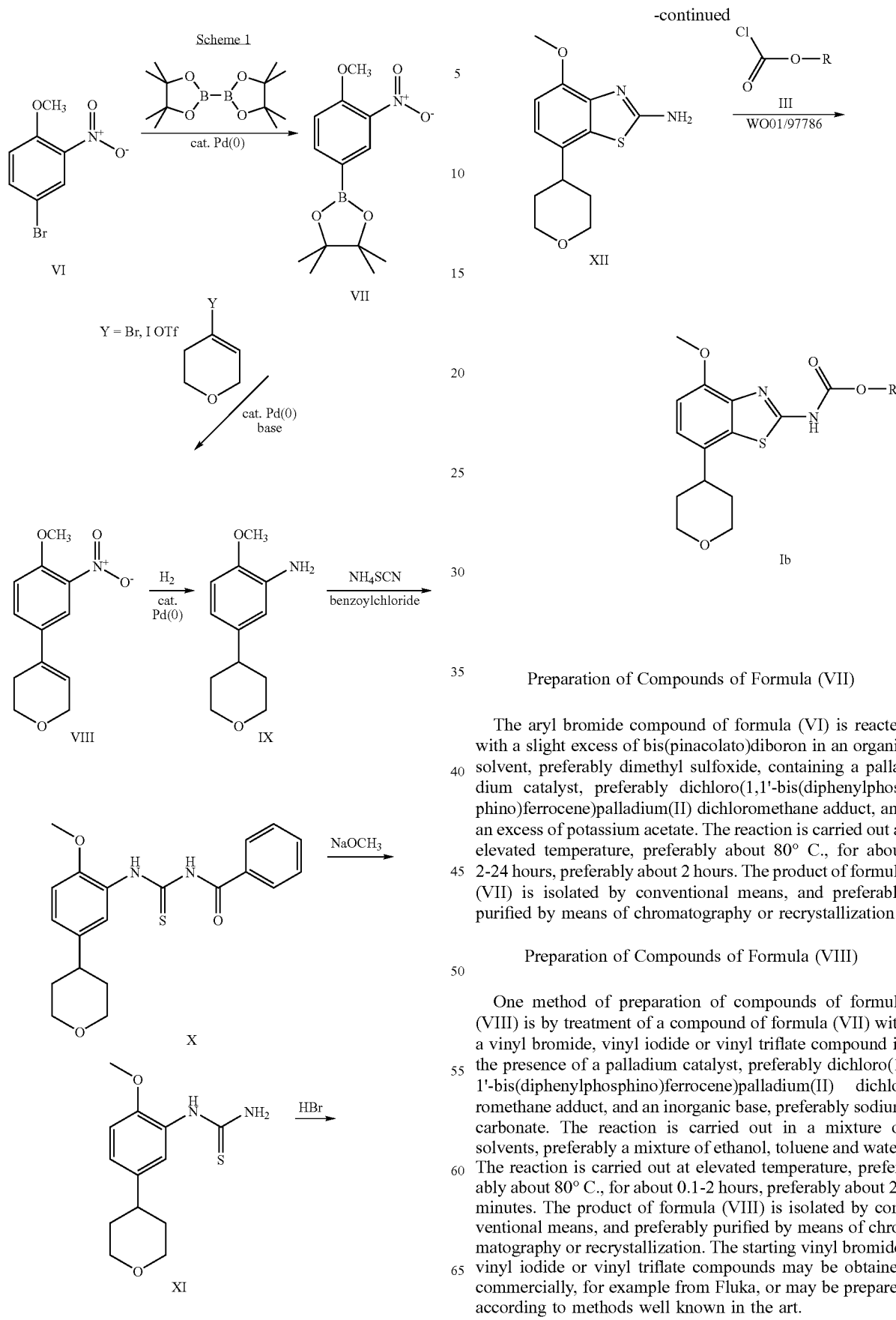

Preparation of Compounds of Formula (VII)

The aryl bromide compound of formula (VI) is reacted with a slight excess of bis(pinacolato)diboron in an organic solvent, preferably dimethyl sulfoxide, containing a palladium catalyst, preferably dichloro(1,1'-bis(diphenylphosphino)ferrocene)palladium(II) dichloromethane adduct, and an excess of potassium acetate. The reaction is carried out at elevated temperature, preferably about 80° C., for about 2-24 hours, preferably about 2 hours. The product of formula (VII) is isolated by conventional means, and preferably purified by means of chromatography or recrystallization.

Preparation of Compounds of Formula (VIII)

One method of preparation of compounds of formula (VIII) is by treatment of a compound of formula (VII) with a vinyl bromide, vinyl iodide or vinyl triflate compound in the presence of a palladium catalyst, preferably dichloro(1,1'-bis(diphenylphosphino)ferrocene)palladium(II) dichloromethane adduct, and an inorganic base, preferably sodium carbonate. The reaction is carried out in a mixture of solvents, preferably a mixture of ethanol, toluene and water. The reaction is carried out at elevated temperature, preferably about 80° C., for about 0.1-2 hours, preferably about 20 minutes. The product of formula (VIII) is isolated by conventional means, and preferably purified by means of chromatography or recrystallization. The starting vinyl bromide, vinyl iodide or vinyl triflate compounds may be obtained commercially, for example from Fluka, or may be prepared according to methods well known in the art.

Preparation of Compounds of Formula (IX)

Compounds of formula (IX) may be prepared by hydrogenation of compounds of formula (VIII) in the presence of a hydrogenation catalyst, preferably 10% palladium on charcoal. These reactions may be carried out in a variety of organic solvents, such as methanol, ethanol, or tetrahydrofuran, preferably methanol, at room temperature and at a pressure of one atmosphere or above, preferably at one atmosphere, for 16-72 hours, preferably about 72 hours. The product of formula (IX) is isolated by conventional means, and preferably purified by means of chromatography or recrystallization.

Preparation of the Compound of Formula (X)

To a solution of ammonium rhodanide in acetone is added benzoyl chloride and a solution of 2-methoxy-5-(tetrahydro-pyran-4-yl)-phenylamine (IX). The reaction is carried out under reflux for about 20 minutes. The product 1-benzoyl-3-[2-methoxy-5-(tetrahydro-pyran-4-yl)-phenyl]-thiourea (X) is isolated by conventional means.

Preparation of the Compound of Formula (XI)

To a solution of 1-benzoyl-3-[2-methoxy-5-(tetrahydro-pyran-4-yl)-phenyl]-thiourea (X) in methanol is added sodium methylate solution and stirring continued for about 1 h at room temperature. The product (XI) [2-methoxy-5-(tetrahydro-pyran-4-yl)-phenyl]-thiourea is isolated by conventional means.

Preparation of the Compound of Formula (XII)

To a solution of 1 [2-methoxy-5-(tetrahydro-pyran-4-yl)-phenyl]-thiourea (XI) in acetic acid is added hydrobromic acid, and stirring continued for about 30 min at 80° C. DMSO is then added dropwise and the reaction mixture stirred for a further 30 min at 80° C. The product (XII) 4-methoxy-7-(tetrahydro-pyran-4-yl)-benzothiazol-2-ylamine is isolated by conventional means.

Preparation of the Compound of Formula (Ib)

4-Methoxy-7-(tetrahydro-pyran-4-yl)-benzothiazol-2-ylamine (XII) is first reacted with phenyl chloroformate as described for (4-methoxy-7-phenyl-benzothiazol-2-yl)-carbamic acid benzyl ester in WO01/97786 and then with N-ethyl-diisopropylamine and a corresponding alcohol of formula HO—R in dimethyl sulfoxide at about 50° C. for 2 h, as illustrated also in scheme 2.

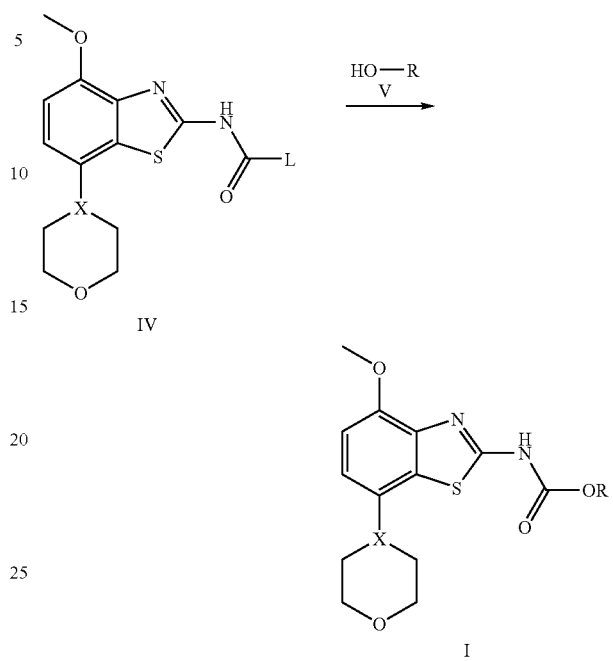

Scheme 2

R and X are as described above, L is a leaving group such as halogen, —O-phenyl or O-lower alkyl.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used.

Salts of Compounds of Formula I

The compounds of formula I may be basic, for example in cases where the residue R contains a basic group such as an aliphatic or aromatic amine moiety. In such cases the compounds of formula I may be converted to a corresponding salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are adenosine receptor ligands and possess a high affinity towards the adenosine $A_{2A}$ receptor.

The compounds were investigated in accordance with the test given hereinafter.

Human Adenosine $A_{2A}$ Receptor

The human adenosine $A_{2A}$ receptor was recombinantly expressed in Chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-SCH-58261 (Dionisotti et al., 1997, Br J Pharmacol 121, 353; 1 nM) binding assay was carried out in 96-well plates in the presence of 2.5 μg of membrane protein, 0.5 mg of Ysi-poly-1-lysine SPA beads and 0.1 U adenosine deaminase in a final volume of 200 μl of buffer A. Non-specific binding was defined using xanthine amine congener (XAC; 2 μM). Compounds were tested at 10 concentrations from 10 μM-0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

The pKi value of compounds of the present application are in the range of 7.6 to 8.7. The most preferred compounds show a pKi>8.0.

| Example No. | $hA_2$ (pKi) |
|---|---|
| 1 | 8.7 |
| 2 | 8.3 |
| 3 | 7.9 |
| 4 | 7.6 |
| 5 | 8.1 |
| 6 | 8.2 |
| 7 | 8.0 |
| 8 | 8.1 |
| 9 | 8.4 |
| 10 | 7.6 |
| 11 | 7.8 |
| 12 | 7.9 |
| 13 | 8.4 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

The most preferred indications in accordance with the present invention are those, which include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| Item | Ingredients | 5 mg | 25 mg | 100 mg | 500 mg |
|---|---|---|---|---|---|
| | | mg/tablet | | | |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | 5 mg | 25 mg | 100 mg | 500 mg |
|---|---|---|---|---|---|
| | | mg/capsule | | | |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The following preparation and examples illustrate the invention but are not intended to limit its scope.

EXAMPLE 1

(trans)-[4-Methoxy-7-(tetrahydro-pyran-4-yl)-benzothiazol-2-yl]-carbamic acid 4-hydroxy-cyclohexyl ester 4-Methoxy-7-(tetrahydro-pyran-4-yl)-benzothiazol-2-ylamine (69 mg, 0.26 mmol) is first reacted with phenyl chloroformate as described for (4-methoxy-7-phenyl-benzothiazol-2-yl)-carbamic acid benzyl ester in WO01/97786 and then with N-ethyl-diisopropylamine (0.090 ml, 0.52 mmol) and (trans)-cyclohexane-1,4-diol (60 mg, 0.52 mmol) in dimethyl sulfoxide (10 ml) at 50° C. for 2 h. Then 100 ml dichoromethane are added, the mixture is extracted with saturated aqueous sodium carbonate and the organic phase is dried and evaporated. Flash-chromatographic purification (silica, eluting with dichloromethane/methanol) yielded the title compound as white solid (7% yield). MS: m/e=407(M+H$^+$), mp 282-284° C. Following the general method of example 1 the compounds of examples 2 to 11 were prepared.

EXAMPLE 2

[4-Methoxy-7-(tetrahydro-pyran-4-yl)-benzothiazol-2-yl]-carbamic acid ethyl ester Using 4-methoxy-7-morpholin-4-yl-benzothiazol-2-ylamine and ethanol, the title compound was obtained as white solid (35% yield). MS: m/e=337(M+H$^+$), mp 170-174° C.

EXAMPLE 3

(4-Methoxy-7-morpholin-4-yl-benzothiazol-2-yl)-carbamic acid 2-methoxy-ethyl ester Using 4-methoxy-7-morpholin-4-yl-benzothiazol-2-ylamine and 2-methoxy-ethanol, the title compound was obtained as off-white solid (52% yield). MS: m/e=368(M+H$^+$), mp 149-152° C.

EXAMPLE 4

(4-Methoxy-7-morpholin-4-yl-benzothiazol-2-yl)-carbamic acid isobutyl ester

Using 4-methoxy-7-morpholin-4-yl-benzothiazol-2-ylamine and isobutanol, the title compound was obtained as yellow crystals (12% yield). MS: m/e=366(M+H$^+$), mp 164-168° C.

EXAMPLE 5

(4-Methoxy-7-morpholin-4-yl-benzothiazol-2-yl)-carbamic acid cyclohexyl ester

Using 4-methoxy-7-morpholin-4-yl-benzothiazol-2-ylamine and cyclohexanol, the title compound was obtained as white solid (60% yield). MS: m/e=392(M+H$^+$), mp 177-179° C.

EXAMPLE 6

(tran)s-(4-Methoxy-7-morpholin-4-yl-benzothiazol-2-yl)-carbamic acid 4-hydroxy-cyclohexyl ester Using 4-methoxy-7-morpholin-4-yl-benzothiazol-2-ylamine and, the title compound was obtained as white foam (14% yield). MS: m/e=408(M+H$^+$), mp 176-179° C. MS: m/e=407.49(M+H$^+$).

EXAMPLE 7

(cis)-(4-Methoxy-7-morpholin-4-yl-benzothiazol-2-yl)-carbamic acid 4-hydroxy-cydohexyl ester Using 4-methoxy-7-morpholin-4-yl-benzothiazol-2-ylamine and (cis)-cydohexane-1,4-diol, the title compound was obtained as colorless crystals (40% yield). MS: m/e=408(M+H$^+$), mp 204-206° C.

EXAMPLE 8

(4-Methoxy-7-morpholin-4-yl-benzothiazol-2-yl)-carbamic acid tetrahydro-pyran-4-yl ester Using 4-methoxy-7-morpholin-4-yl-benzothiazol-2-ylamine and tetrahydropyran-4-ol, the title compound was obtained as white solid (7% yield). MS: m/e=394(M+H$^+$), mp 187-188° C.

EXAMPLE 9

(rac)-(exo,exo)-(4-Methoxy-7-morpholin-4-yl-benzothiazol-2-yl)-carbamic acid 5-hydroxy-bicyclo [2.2.1]hept-2-yl ester Using 4-methoxy-7-morpholin-4-yl-benzothiazol-2-ylamine and (rac)-(exo,exo)-bicyclo[2.2.1]heptane-2,5-diol, the title compound was obtained as white solid (10% yield). MS: m/e=420(M+H$^+$), mp 193-194° C.

EXAMPLE 10

(R)-(4-Methoxy-7-morpholin-4-yl-benzothiazol-2-yl)-carbamic acid tetrahydro-furan-3-yl ester Using 4-methoxy-7-morpholin-4-yl-benzothiazol-2-ylamine and (R)-tetrahydro-furan-3-ol, the title compound was obtained as white crystals (33% yield). MS: m/e=380 (M+H$^+$), mp 198-200° C.

EXAMPLE 11

(cis/trans)-(4-Methoxy-7-morpholin-4-yl-benzothiazol-2-yl)-carbamic acid 3-hydroxy-cyclopentyl ester Using 4-methoxy-7-morpholin-4-yl-benzothiazol-2-ylamine and (cis/trans)-cyclopentane-1,3-diol, the title compound was obtained as white solid (42% yield). MS: m/e=394(M+H$^+$), mp 188-189° C.

EXAMPLE 12

[4-Methoxy-7-(tetrahydro-pyran-4-yl)-benzothiazol-2-yl]-carbamic acid tetrahydro-furan-2-ylmethyl ester Using 7-(tetrahydropyran-4-yl)-4-methoxy-benzothiazol-2-ylamine and (tetrahydro-furan-2-yl)-methanol, the title compound was obtained as white solid (8% yield). MS: m/e=393(M+H$^+$), mp 175-180° C.

EXAMPLE 13

[4-Methoxy-7-(tetrahydro-pyran-4-yl)-benzothiazol-2-yl]-carbamic acid (S)-(tetrahydro-furan-3-yl) ester Using 7-(tetrahydropyran-4-yl)-4-methoxy-benzothiazol-2-ylamine and (S)-etrahydro-furan-3-ol, the title compound was obtained as white solid (13% yield). MS: m/e=379(M+H$^+$), mp 195-200° C.

Intermediates

EXAMPLE 14

4-Methoxy-7-(tetrahydro-pyran-4-yl)-benzothiazol-2-yl-amine (X)

a) 2-(4-Methoxy-3-nitro-phenyl)-4,4,5,5-tetramethyl-[1,3,2]dioxaborolane (VII)

To a stirred solution of 1.30 g (5.60 mmol) 4-bromo-2-nitroanisole (VI) in 25 ml DMSO were added 1.57 g (6.16 mmol) bis(pinacolato)diboron, 123 mg (0.17 mmol) dichloro(1,1'-bis(diphenylphosphino)ferrocene)palladium (II) dichloromethane adduct and 1.65 g (16.8 mmol) potassium acetate. The mixture was heated at 80° C. for 2 h and then cooled to room temperature, poured onto water, and extracted three times with ethyl acetate. The combined organic phases were dried over sodium sulfate and concentrated in vacuo. Flash chromatography (½ ethyl acetate/hexane then ethyl acetate) afforded 1.39 g 2-(4-methoxy-3-nitro-phenyl)-4,4,5,5-tetramethyl-[1,3,2]dioxaborolane (VII) as an off-white solid. ES-MS m/e (%): 280 (M+H$^+$, 100).

b) 4-(4-Methoxy-3-nitro-phenyl)-3,6-dihydro-2H-pyran (VIII)

To a stirred solution of 4.36 g (15.6 mmol) 2-(4-methoxy-3-nitro-phenyl)-4,4,5,5-tetramethyl-[1,3,2]dioxaborolane (VII) and 3.30 g (14.2 mmol) trifluoromethanesulfonic acid 3,6-dihydro-2H-pyran-4-yl ester in 33 ml ethanol and 82 ml toluene was added 580 mg (0.71 mmol) dichloro(1,1'-bis(diphenylphosphino)ferrocene)palladium(II) dichloromethane adduct. The mixture was heated at 80° C. and 16.5 ml (33.0 mmol) 2 M aqueous sodium carbonate solution was added dropwise. The reaction mixture was stirred for 20 minutes at 80° C. and then cooled to room temperature, poured onto water, and extracted three times with ethyl acetate. The combined organic phases were dried over sodium sulfate and concentrated in vacuo. Flash chromatography (¼ ethyl acetate/hexane) afforded 2.00 g (60%) 4-(4-methoxy-3-nitro-phenyl)-3,6-dihydro-2H-pyran (VIII) as a light yellow solid. ES-MS m/e (%): 253 (M+NH$_4^+$, 100), 236 (M+H$^+$, 24).

c) 2-Methoxy-5-(tetrahydro-pyran-4-yl)-phenylamine (IX)

To a stirred solution of 3.30 g (14.0 mmol) 4-(4-methoxy-3-nitro-phenyl)-3,6-dihydro-2H-pyran (VIII) in 70 ml methanol and 70 ml dichloromethane was added a spatula end of 10% palladium on charcoal and the mixture was then stirred for 20 minutes at room temperature under an atmosphere of hydrogen. The mixture was then filtered, washing with dichloromethane, and the filtrate concentrated in vacuo to afford 2.75 g (95%) 2-methoxy-5-(tetrahydro-pyran-4-yl)-phenylamine (IX) as an off-white crystalline solid ES-MS m/e (%): 208 (M+H$^+$, 100).

d) 1-Benzoyl-3-[2-methoxy-5-(tetrahydro-pyran-4-yl)-phenyl]-thiourea (X)

To a stirred solution of 1.11 g (14.6 mmol) ammonium rhodanide in 60 ml acetone was added dropwise 1.54 ml (13.3 mmol) benzoyl chloride and the mixture heated at reflux for 10 minutes. A solution of 2.75 g (13.3 mmol) 2-methoxy-5-(tetrahydro-pyran74-yl)-phenylamine in 30 ml acetone was then added dropwise and the reaction mixture heated at reflux for a further 10 minutes. The mixture was then cooled to room temperature, poured onto sodium bicarbonate solution, and extracted three times with dichloromethane. The combined organic phases were dried over sodium sulfate and concentrated in vacuo. Flash chromatography (1/1 ethyl acetate/hexane) followed by trituration in ether afforded 3.25 g (66%) 1-benzoyl-3-[2-methoxy-5-(tetrahydro-pyran-4-yl)-phenyl]-thiourea as a white solid. ES-MS m/e (%): 371 (M+H$^+$, 100).

e) [2-Methoxy-5-(tetrahydro-pyran-4-yl)-phenyl]-thiourea (XI)

To a stirred solution of 3.25 g (8.77 mmol) 1-benzoyl-3-[2-methoxy-5-(tetrahydro-pyran-4-yl)-phenyl]-thiourea in 45 ml methanol was added dropwise 0.25 ml (1.32 mmol) 5.3 M sodium methylate solution and stirring continued for 1 h at room temperature. The mixture was then poured onto water and extracted three times with ethyl acetate. The combined organic phases were dried over sodium sulfate and concentrated in vacuo. Flash chromatography (ethyl acetate) afforded 1.90 g (81%) [2-methoxy-5-(tetrahydro-pyran-4-yl)-phenyl]-thiourea as a white foam. ES-MS m/e (%): 267 (M+H⁺, 100).

f) 4-Methoxy-7-(tetrahydro-pyran-4-yl)-benzothiazol-2-yl-amine (XII)

To a stirred solution of 1.90 g (7.13 mmol) [2-methoxy-5-(tetrahydro-pyran-4-yl)-phenyl]-thiourea in 20 ml acetic acid heated to 80° C. was added dropwise 1.45 ml (8.27 mmol) hydrobromic acid. (5.7 M solution in acetic acid) and stirring continued for 30 min at 80° C. 0.56 ml (7.85 mmol) DMSO was then added dropwise and the reaction mixture stirred for a further 30 min at 80° C. The mixture was then cooled to room temperature, poured slowly onto sodium bicarbonate solution, and ethyl acetate added. The mixture was stirred for 10 minutes at room temperature and the resulting crystals collected by filtration, washing with ethyl acetate. The mother liquor phases were separated and the organic phase concentrated in vacuo to 5 ml. The resulting second crop of crystals was collected by filtration and combined with the first crop to afford 920 mg (49%) 4-methoxy-7-(tetrahydro-pyran-4-yl)-benzothiazol-2-ylamine as a white solid. ES-MS m/e (%): 265 (M+H⁺, 100).

The invention claimed is:

1. A compound of formula I

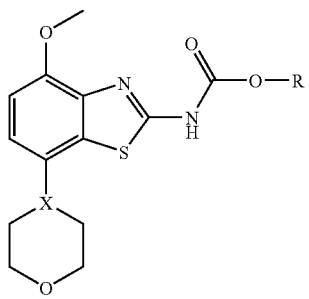

wherein
R is selected from the group consisting of
cyclopentyl,
cyclopentyl substituted by hydroxy,
cyclohexyl,
cyclohexyl substituted by hydroxy,
isobutyl,
methoxyethyl,
tetrahydropyran-4-yl,
—(CH$_2$)$_n$-tetrahydrofuran-2-yl,
—(CH$_2$)$_n$-tetrahydrofuran-3-yl, and
5-hydroxy-bicyclo[2.2.1]hept-2-yl;
X is selected from CH and N; and
n is 0 or 1;
or a pharmaceutically acceptable salt thereof.

2. A compound of formula I

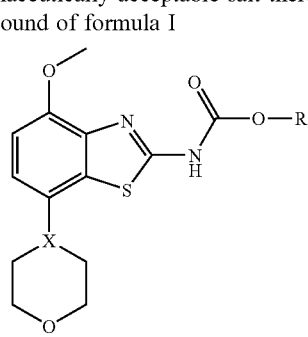

wherein
R is selected from the group consisting of
cyclohexyl substituted by hydroxy,
—(CH$_2$)$_n$-tetrahydrofuran-2-yl, and
—(CH$_2$)$_n$-tetrahydrofuran-3-yl;
X is CH; and
n is 0 or 1;
or a pharmaceutically acceptable salt thereof.

3. A compound of formula I

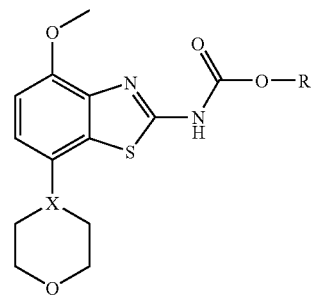

wherein
R is selected from the group consisting of
cyclopentyl substituted by hydroxy,
cyclohexyl,
cydohexyl substituted by hydroxy,
isobutyl,
methoxyethyl,
tetrahydropyran-4-yl,
—(CH$_2$)$_n$-tetrahydrofuran-3-yl, and
5-hydroxy-bicyclo[2.2.1]hept-2-yl;
X is N; and
n is 0 or 1;
or a pharmaceutically acceptable salt thereof.

4. A compound of formula I

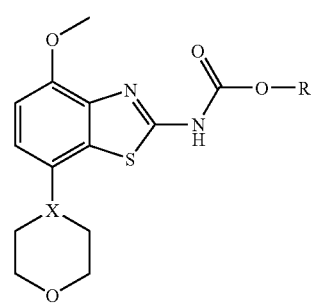

wherein
R is selected from the group consisting of
cydopentyl,
cyclopentyl substituted by hydroxy,
cydohexyl,
cyclohexyl substituted by hydroxy,
isobutyl,
methoxyethyl,
tetrahydropyran-4-yl,
tetrahydrofuran-3-yl, and
5-hydroxy-bicyclo[2.2.1]hept-2-yl;
X is selected from CH and N;
or a pharmaceutically acceptable salt thereof.

5. A compound of formula I in accordance with claim 1, wherein R is selected from the group consisting of
cyclopentyl,
cyclopentyl substituted by hydroxy,
cyclohexyl, and
cydohexyl substituted by hydroxy.

6. The compounds of formula I in accordance with claim 5, which compound is selected from
(trans)-[4-methoxy-7-(tetrahydro-pyran-4-yl)-benzothiazol-2-yl]-carbamic acid 4-hydroxy-cyclohexyl ester,
(4-methoxy-7-morpholin-4-yl-benzothiazol-2-yl)-carbamic acid cyclohexyl ester,
(trans)-(4-methoxy-7-morpholin-4-yl-benzothiazol-2-yl)-carbamic acid 4-hydroxy-cyclohexyl ester,
(cis)-(4-methoxy-7-morpholin-4-yl-benzothiazol-2-yl)-carbamic acid 4-hydroxy-cyclohexyl ester and
(cis/trans)-(4-methoxy-7-morpholin-4-yl-benzothiazol-2-yl)-carbamic acid 3-hydroxy-cyclopentyl ester.

7. The compound of formula I in accordance with claim 1, wherein R is selected from isobutyl and methoxyethyl.

8. The compound of formula I in accordance with claim 7, which compound is
(4-methoxy-7-morpholin-4-yl-benzothiazol-2-yl)-carbamic acid isobutyl ester.

9. The compound of formula I in accordance with claim 1, wherein R is selected from tetrahydropyran-4-yl, —(CH$_2$)$_n$-tetrahydrofuran-2-yl and —(CH$_2$)$_n$-tetrahydrofuran-3-yl.

10. The compound of formula I in accordance with claim 9, which compound is selected from
(4-methoxy-7-morpholin-4-yl-benzothiazol-2-yl)-carbamic acid tetrahydro-pyran-4-yl ester,
(R)-(4-methoxy-7-morpholin-4-yl-benzothiazol-2-yl)-carbamic acid tetrahydro-furan-3-yl ester,
[4-methoxy-7-(tetrahydro-pyran-4-yl)-benzothiazol-2-yl]-carbamic acid tetrahydro-furan-2-yl-methyl ester, and
[4-Methoxy-7-(tetrahydro-pyran-4-yl)-benzothiazol-2-yl]-carbamic acid (S)-(tetrahydro-furan-3-yl)ester.

11. The compound of formula I in accordance with claim 1, wherein R is 5-hydroxy-bicyclo[2.2.1]hept-2-yl.

12. The compound of formula I in accordance with claim 10, which compound is
(rac)-(exo,exo)-(4-methoxy-7-morpholin-4-yl-benzothiazol-2-yl)-carbamic acid 5-hydroxy-bicyclo[2.2.1]hept-2-yl ester.

13. A process for preparing a compound of formula I as defined in claim 1, which process comprises reacting a compound of formula

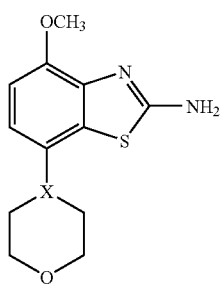

II with a compound of formula

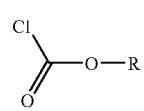

III to produce a compound of formula

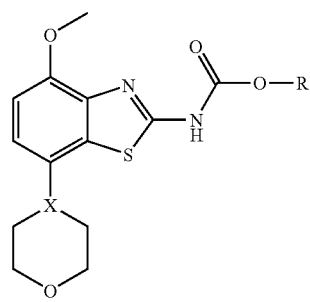

I wherein
R is selected from the group consisting of
cyclopentyl,
cyclopentyl substituted by hydroxy,
cyclohexyl,
cyclohexyl substituted by hydroxy,
isobutyl,
methoxyethyl,
tetrahydropyran-4-yl,
—(CH$_2$)$_n$-tetrahydrofuran-2-yl,
—(CH$_2$)$_n$-tetrahydrofuran-3-yl, and
5-hydroxy-bicyclo[2.2.1]hept-2-yl;
X is selected from CH and N.

14. A process for preparing a compound of formula I as defined in claim 1, which process comprises reacting a compound of formula

IV with a compound of formula

HO—R   V to produce a compound of formula

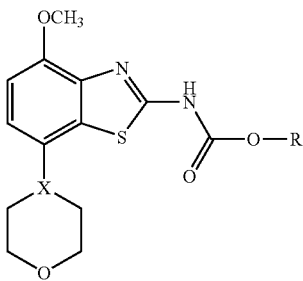

wherein
R is selected from the group consisting of
cyclopentyl,
cyclopentyl substituted by hydroxy,
cyclohexyl,
cyclohexyl substituted by hydroxy,
isobutyl,
methoxyethyl,
tetrahydropyran-4-yl,
—(CH$_2$)$_n$-tetrahydrofuran-2-yl,
—(CH$_2$)$_n$-tetrahydrofuran-3-yl, and
5-hydroxy-bicyclo[2.2.1]hept-2-yl;
X is selected from CH and N; and
L is a leaving group selected from the group consisting of halogen, —O-phenyl and O-lower alkyl.

15. The process of claim 13, which further comprises converting the compound obtained into a pharmaceutically acceptable salt.

16. The process of claim 14, which further comprises converting the compound obtained into a pharmaceutically acceptable salt.

17. A pharmaceutical composition which comprises a compound of formula I

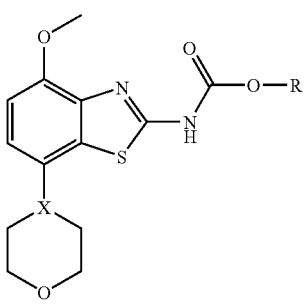

wherein
R is selected from the group consisting of
cyclopentyl,
cyclopentyl substituted by hydroxy,
cyclohexyl,
cyclohexyl substituted by hydroxy,
isobutyl,
methoxyethyl,
tetrahydropyran-4-yl,
—(CH$_2$)$_n$-tetrahydrofuran-2-yl,
—(CH$_2$)$_n$-tetrahydrofuran-3-yl, and
5-hydroxy-bicyclo[2.2.1]hept-2-yl;
X is selected from CH and N; and
n is 0 or 1;
or a pharmaceutically acceptable salt thereof,
and a pharmaceutical acceptable carrier.

18. A method of treating a disease selected form Alzheimer's disease, depression, Parkinson's disease and ADHD comprising administering to a patient in need of such treatment a therapeutically effective amount of at least one compound of formula I

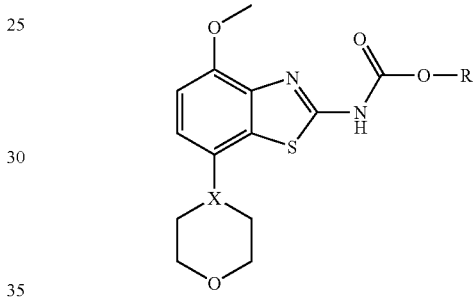

wherein
R is selected from the group consisting of
cyclopentyl,
cyclopentyl substituted by hydroxy,
cyclohexyl,
cyclohexyl substituted by hydroxy,
isobutyl,
methoxyethyl,
tetrahydropyran-4-yl,
—(CH$_2$)$_n$-tetrahydrofuran-2-yl,
—(CH$_2$)$_n$-tetrahydrofuran-3-yl, and
5-hydroxy-bicyclo[2.2.1]hept-2-yl;
X is selected from CH and N; and
n is 0 or 1;
or a pharmaceutically acceptable salt thereof.

19. A compound according to claim 1 wherein R is cyclohexyl substituted by hydroxy and X is CH.

* * * * *